United States Patent [19]

Geiss

[11] 4,363,323

[45] Dec. 14, 1982

[54] NASOGASTRIC TUBE ADAPTED TO AVOID PRESSURE NECROSIS

[76] Inventor: Alan C. Geiss, 50 Brampton La., Great Neck, N.Y. 11023

[21] Appl. No.: 213,028

[22] Filed: Dec. 4, 1980

[51] Int. Cl.[3] .......... A61M 25/00

[52] U.S. Cl. .......... 604/281; 128/207.18; 604/45

[58] Field of Search .......... 128/207.14–207.18, 128/348–350, 133

[56] References Cited

U.S. PATENT DOCUMENTS

| | | | |
|---|---|---|---|
| 402,285 | 4/1889 | Sutton | 128/228 |
| 3,169,528 | 2/1965 | Knox et al. | 128/350 R |
| 3,189,031 | 6/1965 | Andersen | 128/350 R |
| 3,409,224 | 11/1968 | Harp et al. | 239/33 |
| 3,599,642 | 8/1971 | Tindel | 128/207.14 |
| 3,942,528 | 3/1976 | Loeser | 128/DIG. 26 |
| 3,964,488 | 6/1976 | Ring et al. | 128/207.14 |
| 4,050,466 | 9/1977 | Koerbacher | 128/207.14 |
| 4,275,724 | 6/1981 | Behrstock | 128/207.14 |

*Primary Examiner*—Dalton L. Truluck

[57] ABSTRACT

A nasogastric tube which includes an intermediate portion for placement adjacent the patient's nostril and capable of assuming and retaining an axial bend. After the tube has been placed, the physician bends the intermediate portion upwardly to direct the tube away from the patient's mouth. As the tube retains the angle to which it has been bent, it is not necessary to retain the bend by taping the tube to the nasal alae and, thus, the possibility of pressure necrosis due to the forces exerted by the bend in the tube is avoided.

11 Claims, 7 Drawing Figures

FIG. 4
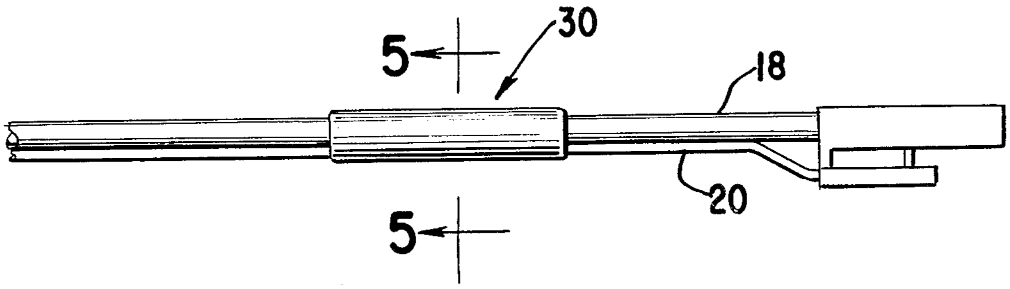
FIG. 5
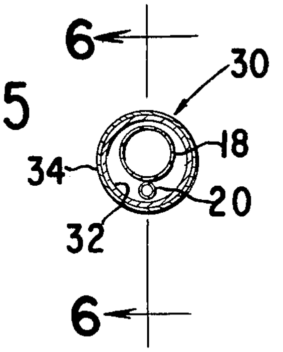
FIG. 7
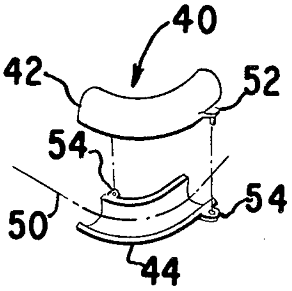
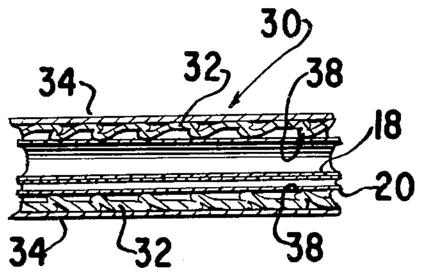
FIG. 6

NASOGASTRIC TUBE ADAPTED TO AVOID PRESSURE NECROSIS

BACKGROUND OF THE INVENTION

The present invention relates generally to nasogastric tubes, for example, used for aspirating fluids from the gastrointestinal tract, or as feeding tubes. More particularly, the present invention relates to novel nasogastric tube designs which avoid the possibility of pressure necrosis of the nasal alae.

Indwelling nasogastric tubes find clinical use for removing accumulated fluids from the gastrointestinal tract due to intestinal obstruction and consequent to decreased gastrointestinal function following abdominal surgery or disease. Indwelling nasogastric tubes are also used for feeding tubes.

The physician introduces the nasogastric tube through one nostril, through the oropharynx and through the esophagus into the stomach (for aspirating fluods) or duodenum (for feeding). The proximal end of the tube thus projects from the nostril for attachment to a suctioning device or to an enteral feeding apparatus. As the tube exits the nostril, it is pulled to the side of the patient's head in an upward direction to avoid interference with the mouth and for patient comfort. To hold the tube in this position, the physician tapes it to the alae or nostril of the nose.

The nasal alae have a tenuous blood supply and, therefore, are prone to developing necrosis due to pressure exerted by the tube held in this fashion. Necrosis can develop within twelve hours after the tube has been placed.

SUMMARY

In one illustrative embodiment of the present invention, a nasogastric tube comprises an elongated tube having a distal end having at least one port for communicating fluids to or from the gastrointestinal tract and a proximal end adapted for communicating such fluids to or from a device exterior to a patient. The elongated tube further comprises an intermediate portion for placement adjacent the patient's nostril and capable of assuming and retaining an axial bend. Accordingly, after the nasogastric tube has been inserted and placement has been checked, the physician bends the intermediate portion adjacent the nostril to the desired angle. As the tube retains the angle to which it has been bent, it is not necessary to maintain the bend by taping the tube to the alae and, thus, the possibility of pressure necrosis due to the forces exerted by the bend in the tube is avoided.

In accordance with a further embodiment of the present invention, a sleeve is adapted to fit over a portion of the tube adjacent the patient's nostril. The sleeve is capable of assuming and retaining an axial bend.

In accordance with still another embodiment of the present invention, a sleeve is provided having an axial bend. The sleeve is adapted to be placed over a portion of the tube adjacent the patient's nostril to impart an axial bend to the tube. Preferably, the sleeve is made in two sections capable of being placed over the tube and joined together after placement of the tube in the patient. The sleeve, accordingly, can be made of inexpensive plastic by well known molding techniques.

In accordance with a method of placing a nasogastric tube in a patient in accordance with the present invention. The tube is inserted through the patient's nostril, through the oropharynx and esophagus and into the stomach. A sleeve is applyed to a portion of the tube adjacent the patient's nostril to bend the tube away from the patient's mouth.

BRIEF DESCRIPTION OF THE DRAWINGS

The present invention, as well as further objects and fearures thereof, will be understood more clearly and fully from the following description of certain preferred embodiments and methods, when read with reference to the accompanying drawings, in which:

FIG. 4 is a diagrammatic view of a further embodiment of the present invention;

FIG. 5 is a cross-sectional view taken along lines 5—5 of FIG. 4;

FIG. 6 is a cross-sectional view taken along lines 6—6 of FIG. 5; and FIG. 7 is an exploded view of a further embodiment of the present invention.

DESCRIPTION OF CERTAIN PREFERRED EMBODIMENTS

Figure 1:
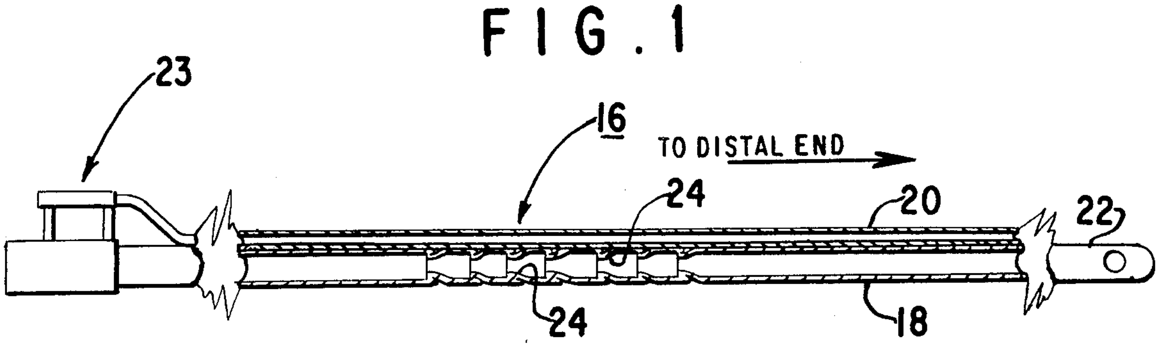
FIG. 1 is a cross-sectional view of an axial portion of a nasogastric tube in accordance with the present invention.

FIG. 1 shows an axial section 16 of a double-lumen nasogastric tube, in cross-section. Double-lumen nasogastric tubes are shown in the Harold W. Anderson U.S. Pat. No. 3,114,373, the entire disclosure of which is incorporated herein by reference. The nasogastric tube of FIG. 1 has a larger aspiration tube 18 and a smaller sump tube 20 in parallel relation with tube 18. The nasogastric tube of FIG. 1 has a distal end 22 having at least one port for communicating fluids to or from the gastrointestinal tract, for example, as shown in U.S. Pat. No. 3,114,373. Preferably, the distal end of the nasogastric tube is constructed in accordance with the teachings of the patent application of Alan C. Geiss et al. entitled "Device for Aspirating Fluids from a Body Cavity or Hollow Organ" and filed concurrently herewith. The nasogastric tube of FIG. 1 is further provided with a proximal end 23 adapted for communicating fluids to or from a device exterior to the patient, such as a suction device coupled to aspiration tube 18.

Figure 2:
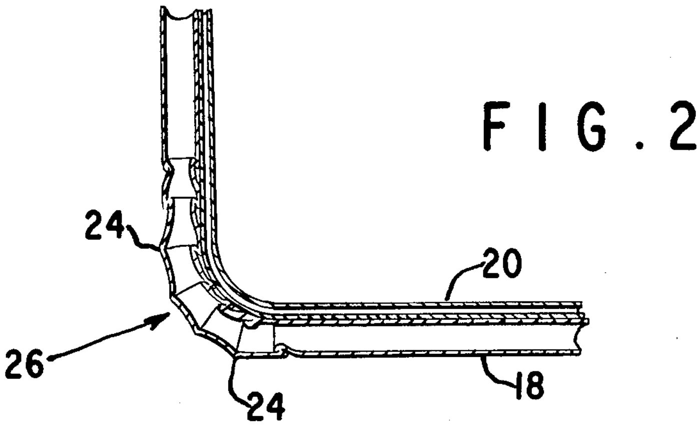
FIG. 2 is a further cross-sectional view of the embodiment of FIG. 1 showing how the portion of the tube assumes and retains an axial bend.

A number of folds 24 are arranged in axially spaced relation in an intermediate portion 26 of tube 18. Folds 24 are directed radially inwardly and project generally toward the proximal end of tube 18, thus to create a bias against outward deformation. However, tube 18 is made of flexible plastic, for example, polyethylene, such that the portion 26 can be bent axially as shown in FIG. 2. Upon the application of sufficient force bending portion 26, a radial sector of each of several folds 24 is forced to deform radially outwardly. The tube 18 resists the axial bend thus to compress the outwardly projecting folds 24. This compressive force, however, tends to force the projecting folds 24 outwardly against their tendency to reassume their original shape, such that they resist further outward disposition, thus causing the portion 26 of tube 18 to retain its bend. Tube 20 is also made of flexible plastic permitting it to bend with tube 18.

The folds 24 are constructed, for example, by heat formation. By virtue of the projection of folds 24 toward the proximal end of the nasogastric tube, particles aspirated from the gastrointestinal tract tend to pass over the inner surfaces of folds 24, rather than being caught therein.

In place of folds 24, portion 26 may be made of a material capable of assuming and retaining an axial bend. In the alternative, an insert of such a material, for example, a metal cylinder, can be placed within portion 26 in order to retain the bend thereof.

Figure 3:
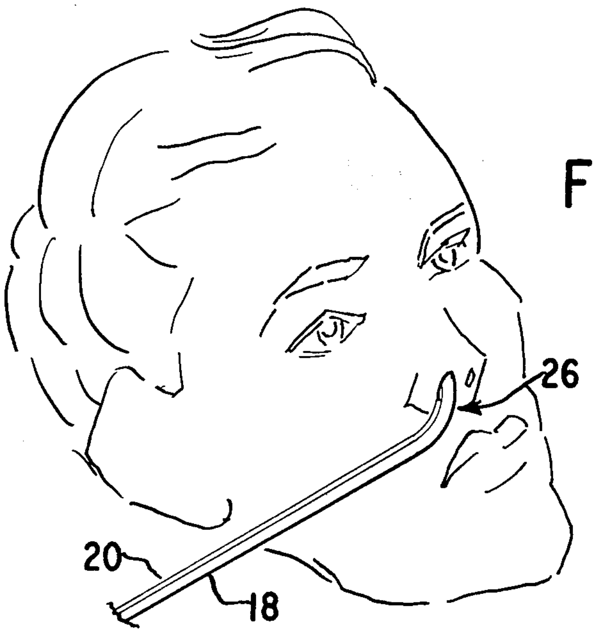
FIG. 3 shows a nasogastric tube according to FIGS. 1 and 2 after placement thereof in a patient.

FIG. 3 illustrates the placement of the nasogastric tube of FIGS. 1 and 2 in the patient. With the portion 26 unbent, the distal end of the tube is introduced through one nostril, through the oropharynx and esophagus into the stomach. In the case of a feeding tube, the distal end is passed through the stomach into the duodenum. When the tube has been thus inserted and the placement has been checked by the physician, he bends the portion 26 of the tube axially to the desired angle, as shown in FIG. 3, to direct the tube away from the patient's mouth.

FIGS. 4, 5 and 6 illustrate a further embodiment of the invention, wherein elements corresponding to those shown in FIGS. 1, 2 and 3 are identified by the same reference numerals. A sleeve 30 is slidably mounted over tubes 18 and 20. Sleeve 30 is adapted to assume and retain an axial bend. Accordingly, the physician first slides sleeve 30 to a point adjacent the proximal end of the nasogastric tube. After the distal end of the tube has been inserted in the manner described with respect to FIG. 3 and placement has been checked, he slides sleeve 30 over tubes 18 and 20 to a position adjacent the patient's nostril. Then he bends sleeve 30 to the desired angle which thereby directs the tube away from the patient's mouth.

As shown in FIG. 6, sleeve 30 has an inner layer 32 and an outer layer 34. Inner layer 32 is comprised of a flexible material having a plurality of folds 38 positioned radially inwardly and similar to folds 24 of FIGS. 1 and 2. Accordingly, folds 38 are capable of being deformed outwardly along a radial sector thereof upon bending the sleeve 30 axially such that the outwardly disposed folds resist an inward deformation. Outer layer 38 is made of a smooth, flexible material, such as a siliconized plastic, to permit sleeve 30 to rest against the patient's skin without causing discomfort to the patient.

FIG. 7 shows a further embodiment of the present invention wherein a sleeve 40 is preformed to have an axial bend and is made of two sections 42 and 44 adapted to be placed over a portion of the tube, indicated by phantom line 50, and joined together adjacent the patient's nostril to impart an axial bend to the tube after placement thereof in the patient as described hereinabove. The two sections 42 and 44 of the FIG. 7 embodiment are held together with two snaps comprising projecting members 52 on section 42 and receptacles 54 in section 44 aligned with projecting members 52 and configured such that members 52 may be snapped into and held within the respective ones of receptacles 54. Accordingly, sections 42 and 44 may be constructed of inexpensive plastic by well known plastic molding techniques. The embodiments of FIGS. 4 through 7 are readily implemented with existing nasogastric tube designs.

Various other good embodiments of sleeves useful in practicing the present invention will be apparent to those of skill in the art upon a perusal of the present disclosure. For example, a sleeve having an axial slot may be provided through which the tube may be passed and which then may be closed.

The terms and expressions which have been employed are used as terms of description and not of limitation, and there is no intention in the use of such terms and expressions of excluding any equivalents of the features shown and described or portions thereof, it being recognized that various modifications are possible within the scope of the invention claimed.

I claim:

1. A nasogastric tube, comprising:

an elongated tube having a distal end and a proximal end;

the tube having sufficient length to permit placement of the distal end in a patient's gastrointestinal tract while the tube extends therefrom through the patient's esophagus and nostril to its proximal end outside the patient's body;

the distal end having at least one port for communicating fluids to or from the gastrointestinal tract and the proximal end being adapted for communicating such fluids to or from a device exterior to the patient;

the elongated tube further having an intermediate portion spaced axially from the distal end to extend through the patient's nostril for placement adjacent the patient's nostril when the tube is in place in the gastrointestinal tract for communicating fluids to or from the tract; and means in said intermediate portion for assuming and retaining an axial bend;

whereby the tube may be fixedly bent to extend from the patient's nostril in a desired direction without affixation to the nose to maintain said bend, to thereby avoid the possibility of pressure necrosis in the nose due to force exerted by the bend in the tube.

2. The nasogastric tube of claim 1, wherein the intermediate portion comprises at least one radially inward fold capable of being deformed outwardly along a radial sector thereof upon bending the intermediate portion axially such that the outwardly disposed fold resists an inward deformation, whereby the axial bend of the intermediate portion is retained.

3. The nasogastric tube of claim 1 or 2, wherein the elongated tube is an aspirating tube and the nasogastric tube further comprises a sump tube in parallel relation with the elongated tube.

4. The nasogastric tube of claim 1, wherein the intermediate portion comprises an insert within the tube and made of a material capable of assuming the shape of and retaining an axial bend of the elongated tube.

5. A nasogastric tube comprising:

an elongated tube having a distal end and a proximal end;

the tube having sufficient length to permit placement of the distal end in a patient's gastrointestinal tract while the tube extends therefrom through the patient's esophagus and nostril to its proximal end outside the patient's body;

the distal end having at least one port for communicating fluids to or from the gastrointestinal tract and the proximal end being adapted for communicating such fluids to or from a device exterior to the patient;

the elongated tube further having an intermediate portion spaced axially from the distal end to extend through the patient's nostril when the tube is in place in the gastrointestinal track for communicating fluids to or from the tract; and a sleeve adapted to fit over the intermediate protion of the tube adjacent the patient's nostril and capable of assuming and retaining an axial bend to thereby impart an axial bend to said portion of the tube;

whereby the tube may be fixedly bent to extend from the patient's nostril in a desired direction without affixation to the nose to maintain said bend, to thereby avoid the possibility of pressure necrosis in the nose due to force exerted by the bend in the tube.

6. The nasogastric tube of claim 5, wherein the sleeve is slidably mounted on the tube.

7. The nasogastric tube of claim 5 or 6, wherein the sleeve has at least one radially inward fold capable of being deformed outwardly along a radial sector thereof upon bending the sleeve axially such that the outwardly disposed fold resists an inward deformation.

8. The nasogastric tube of claim 7, wherein the sleeve further comprises a flexible outer layer having a smooth outer surface for resting against the patient's skin.

9. A nasogastric tube having a distal end and a proximal end;

the tube having sufficient length to permit placement of the distal end in a patient's gastrointestinal tract while the tube extends therefrom through the patient's esophagus and nostril to its proximal end outside the patient's body;

the distal end having at least one port for communicating fluids to or from the gastrointestinal tract and the proximal end being adapted for communicating such fluids to or from a device exterior to the patient;

the elongated tube further having an intermediate portion spaced axially from the distal end to extend through the patient's nostril when the tube is in place in the gastrointestinal tract for communicating fluids to or from the tract; and a sleeve having an axial bend and adapted to be placed over the intermediate portion of the tube adjacent the patient's nostril to impart an axial bend to the tube;

whereby the tube may be fixedly bent to extend from the patient's nostril without affixation to the nose to maintain said bend, to thereby avoid the possibility of pressure necrosis in the nose due to the force exerted by the bend in the tube.

10. The nasogastric tube of claim 9, wherein the sleeve comprises two sections capable of being placed over the tube and joined together after placement of the tube in the patient.

11. A method for placing the nasogastric tube of claim 5 or 9 in a patient, comprising the steps of:

inserting the tube through the patient's nasopharynx, through the oropharynx and esophagus and into the stomach such that the intermediate portion of the tube is positioned adjacent the patient's nostril; and applying said sleeve to said intermediate portion of the tube adjacent the patient's nostril to bend the tube away from the patient's mouth.

* * * * *